US00PP36999P2

(12) United States Plant Patent
Seto

(10) Patent No.: US PP36,999 P2
(45) Date of Patent: Oct. 7, 2025

(54) ***HYDRANGEA* PLANT NAMED 'Naga 4'**

(50) Latin Name: *Hydrangea serrata*
Varietal Denomination: Naga 4

(71) Applicant: Osco Garden B.V., Aalsmeer (NL)

(72) Inventor: Yasuhiko Seto, Sizuoka (JP)

(73) Assignee: OSCO GARDEN B.V., Aalsmeer (NL)

( * ) Notice: Subject to any disclaimer, the term of this patent is extended or adjusted under 35 U.S.C. 154(b) by 0 days.

(21) Appl. No.: 18/953,047

(22) Filed: Nov. 19, 2024

Related U.S. Application Data

(60) Provisional application No. 63/618,888, filed on Jan. 8, 2024.

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

(56) References Cited

U.S. PATENT DOCUMENTS

PP25,535 P2 * 5/2015 Zampini ..... A01H 6/48
Plt./250

* cited by examiner

*Primary Examiner* — Shubo Zhou
*Assistant Examiner* — Zachariah Allan Kay
(74) *Attorney, Agent, or Firm* — Penny J. Aguirre

(57) ABSTRACT

A new cultivar of *Hydrangea* serrata plant named 'Naga 4' that is characterized by its unique foliage colors; young foliage in summer is tri-color green with white margins and flushed with bright pink and mature foliage that is green with white margins, its blooms present from mid-June to August in The Netherlands, its pink flower buds that open into pink flowers with a light pink and white centers, and its suitability as a container plant.

3 Drawing Sheets

Botanical classification: *Hydrangea serrata.*
Varietal denomination: 'Naga 4'.

BACKGROUND OF THE INVENTION

The present invention relates to a new and distinct cultivar of *Hydrangea serrata* and will be referred to hereafter by its cultivar name, 'Naga 4'. 'Naga 4' represents a new cultivar of mountain *Hydrangea,* a perennial shrub grown for landscape use and as a potted plant.

'Naga 4' was discovered as a chance seedling that was growing in a trial field of unnamed and unpatented proprietary plants of *Hydrangea serrata* in the Inventor's breeding program in June of 2013 Gotenba-City, Sizuoka, Japan. The parents are unknown.

Asexual propagation of the new cultivar was first accomplished by softwood stem cuttings by the Inventor in June of 2017 in Gotenba-City, Sizuoka, Japan. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Naga 4' as a unique cultivar of *Hydrangea.*

1. 'Naga 4' exhibits unique foliage colors; young foliage in summer is tri-color green with white margins and flushed with bright pink, mature foliage is green with white margins.

2. 'Naga 4' exhibits blooms from mid-June to August in The Netherlands.
3. 'Naga 4' exhibits pink flower buds with sterile flowers sepals that open with pink margins and light pink and white centers.
4. 'Naga 4' exhibits suitability as a container plant.

'Naga 4' can be most closely compared to the *Hydrangea serrata* cultivars 'Aihime' (not patented) and 'Pink Petticoat' (not patented). 'Aihime' is similar to 'Naga 4' in having unique colored foliage. 'Aihime' differs from 'Naga 4' in having foliage that is non-variegated and green with a gold cast and red tinged young foliage, fewer spots on the stems, and sterile flower sepals that one color. 'Pink Petticoat' is similar to 'Naga 4' in having suitability as a container plant and sterile flowers with pink sepals. 'Pink Petticoat' differs from 'Naga 4' in having lighter pink flowers, and foliage that is all green in color that becomes dark red in autumn.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102 (b) (1) for disclosure and/or sales prior to the filing date but less than one year prior to the effective filing date. Disclosures include website listings by Chelsea Flower Show, Royal Horticulture Society, Thompson and Morgan, Dobies, Van Meuwen, Pinterest, Cowell's Garden Centre, Instagram, Good Housekeeping, R.H.S. Plants, Plantarium, FlorAccess, QVC UK, Waitrose Garden, Crocus, YouTube, The Big Plant Nursery, Coolings Garden Centre, Gardenform, Ebay, megapolis2021, BBC, Jespers Panteskole, Groupon, Planttip BV, Facebook, Сем Ca д, Baldur-Garten, Fabricut, Nezabravke Flowers, Yahoo News, Dzungla Plants, 123Zimmerpflanzen, Wowcher, Amazon, TikTok, Landgard, JBPlantes, House Beautiful, Home and Texture, pagescdn, ikp Pressecenter, The Blackberry Garden, FloraXchange, Trajnice Carniola, Suttons Gardening Grow How, PlatformGroen, Beyond the Garden Gates, Gardens Illustrated, LinkedIn, De Hovenier, Van Son & Koot, Mr Fothergills UK, and Osco Garden BV.

BRIEF DESCRIPTION OF THE DRAWINGS

The accompanying color photographs illustrate the overall appearance and distinct characteristics of the new *Hydrangea.* The photographs were taken of a three-year-old plant of 'Naga 4' as grown outdoors in a 28-cm container Kaatsheuvel, The Netherlands.

The photograph in FIG. 1 provides a side view of the plant habit of 'Naga 4' in bloom.

Figure 1:
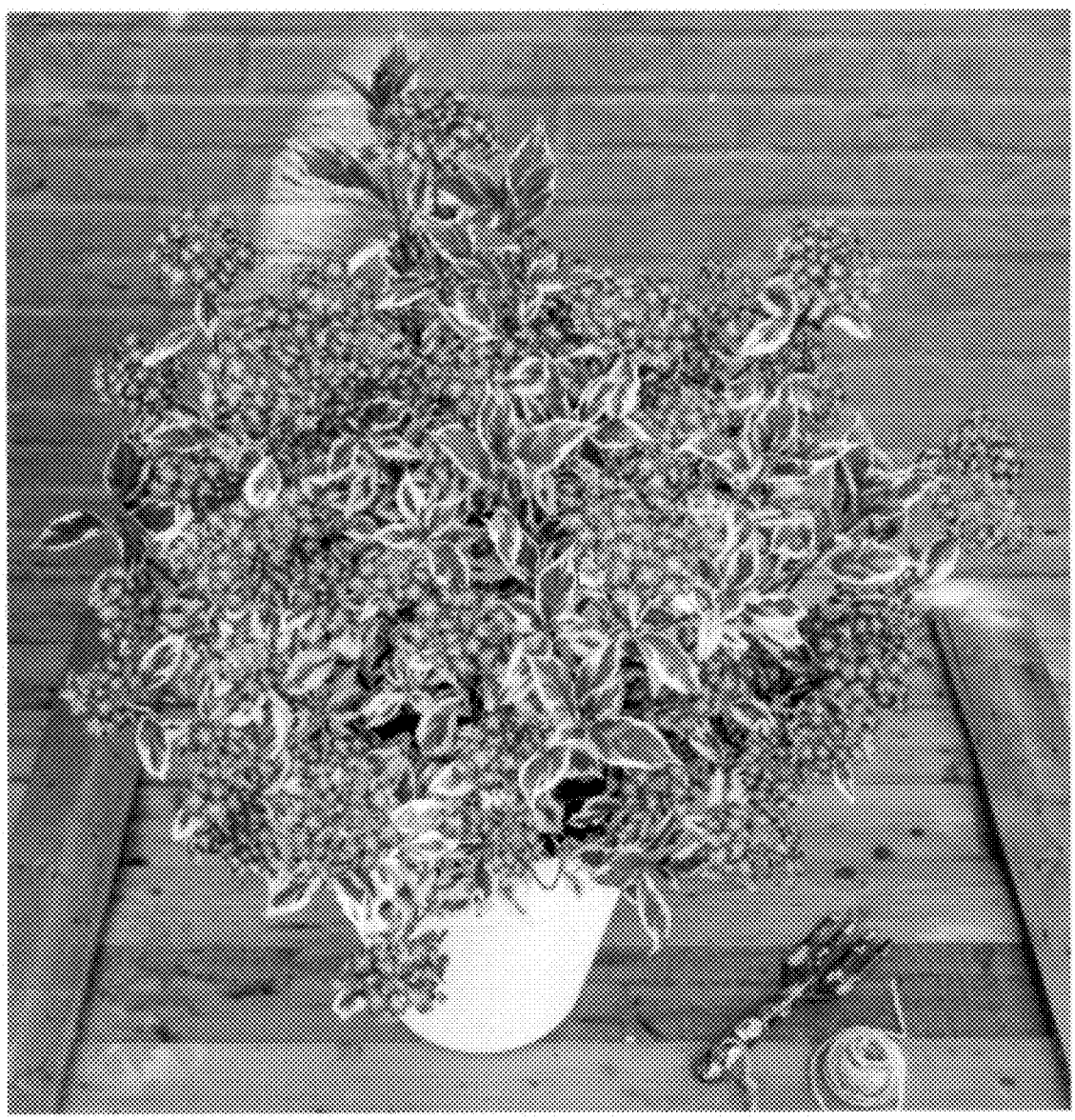
Figure 2:
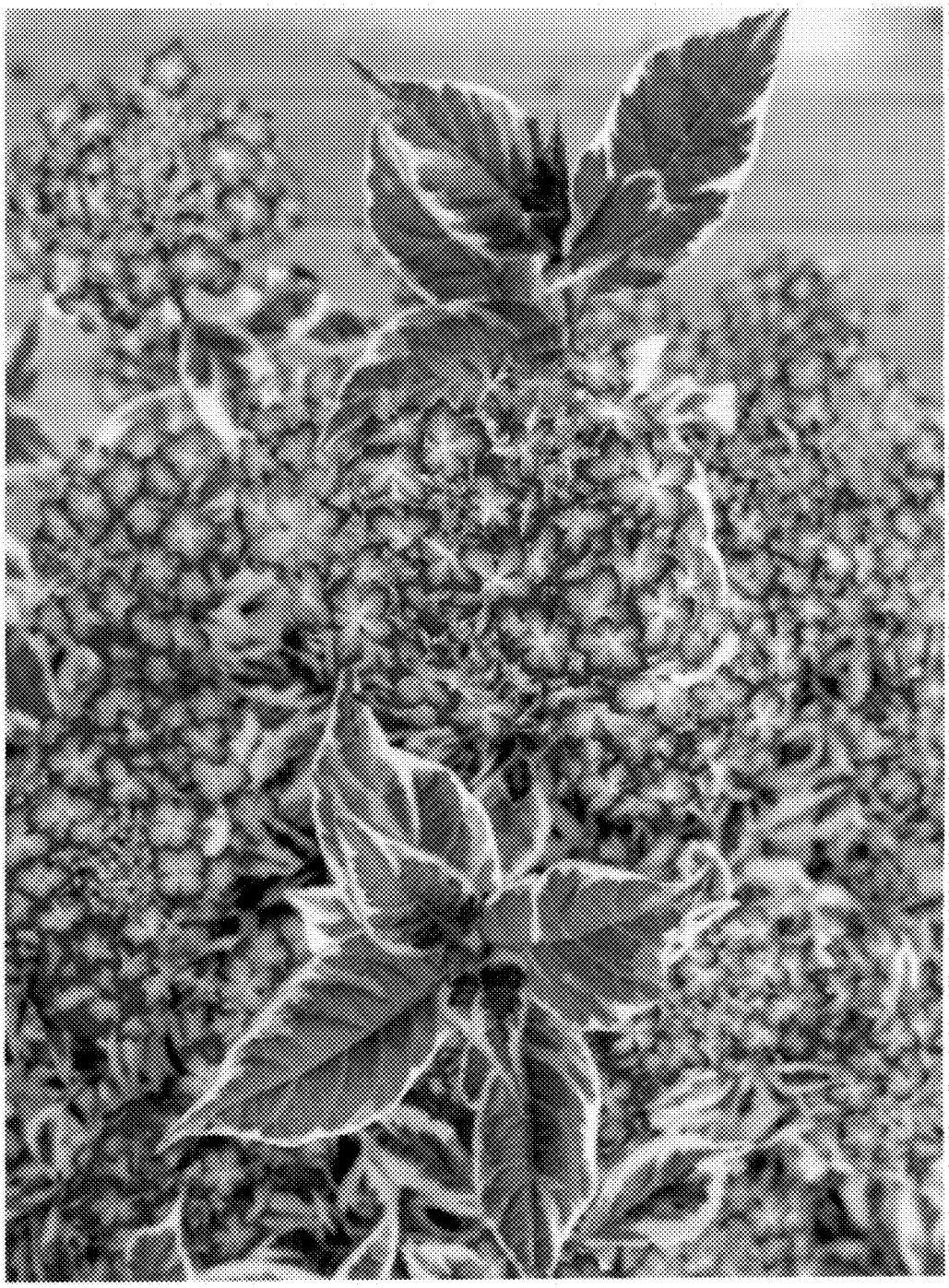

The photograph in FIG. 2 provides a close-up view of fully open inflorescences and the foliage of 'Naga 4'.

Figure 3:
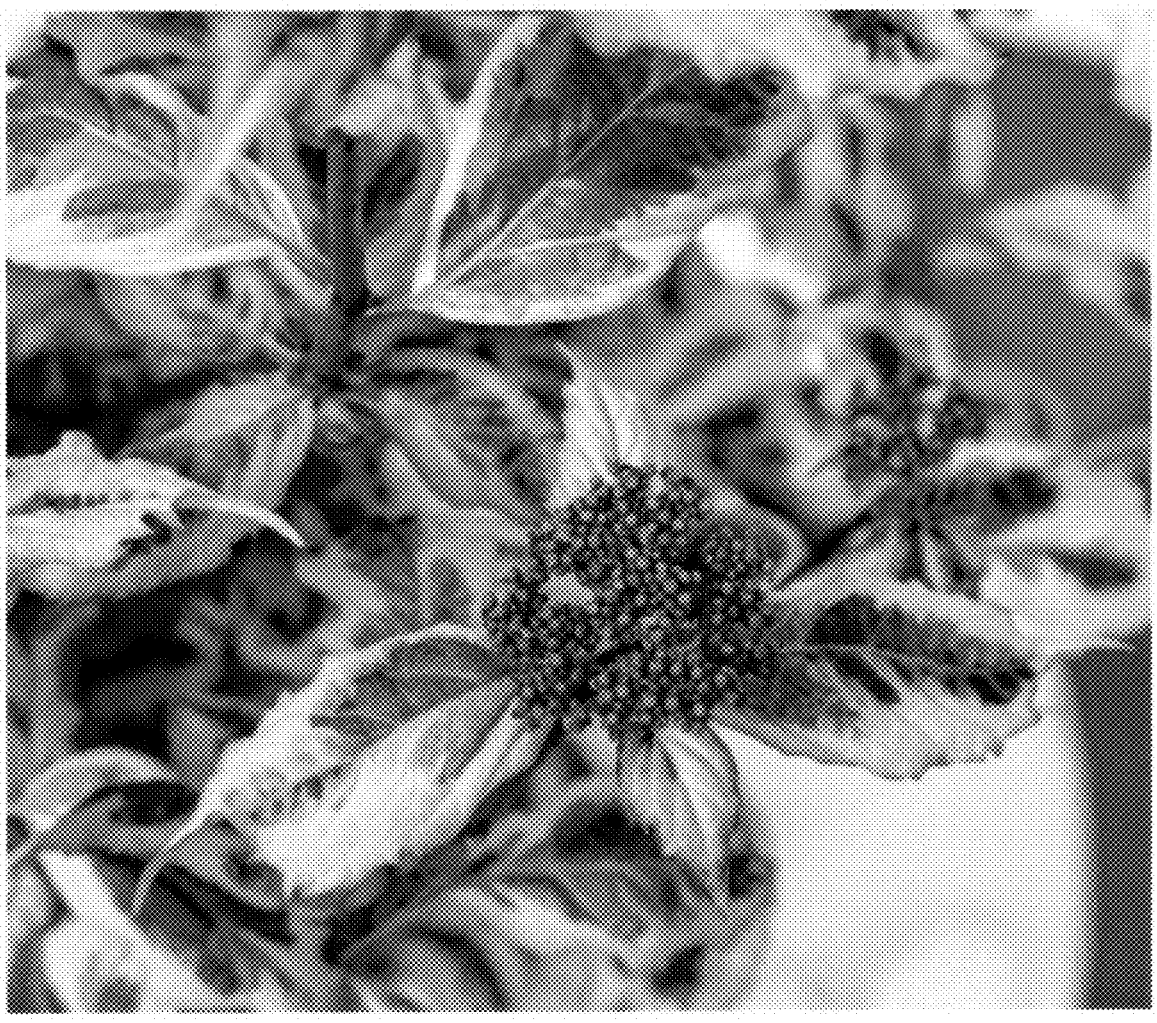

The photograph in FIG. 3 provides a close-up view of a young inflorescence of 'Naga 4' in the summer.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of 3-year-old plants of 'Naga 4' as grown outdoors in Kaatsheuvel, The Netherlands. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—Mid-July into August in The Netherlands.

*Plant type.*—Deciduous shrub.

*Plant habit.*—Low growing and spreading upright, nearly groundcover-like.

*Height and spread.*—1 m in height and width as a mature plant in the landscape.

*Cold hardiness.*—At least in U.S.D.A. Zone 6.

*Diseases and pests.*—No susceptibility and resistance to diseases or pests has been observed.

*Root description.*—Fine, fibrous and dense, NN155A and 164A in color.

*Propagation.*—Softwood stem cuttings.

*Root development.*—An average of 5 to 6 weeks for root initiation with a young plant produced in 4 to 5 months from a rooted cutting.

*Growth rate and vigor.*—Moderate.

Stem description:

*Stem shape.*—Rounded.

*Stem strength.*—Strong.

*Stem color.*—Young; 144A, mature and old bark; N199B.

*Stem size.*—Average of 43 cm in length and 4 mm in diameter.

*Stem surface.*—Young; slightly glossy, slightly pubescent and covered with lenticels 1 to 2 mm in diameter, older stems and bark glabrous, slightly glossy.

*Stem aspect.*—Upright, average angle of 55° to soil level.

*Internode length.*—An average of 4 cm.

*Branching.*—Freely branched from the base with an average of 30 lateral branches.

Foliage description:

*Leaf shape.*—Ovate.

*Leaf arrangement.*—Opposite.

*Leaf division.*—Simple.

*Leaf base.*—Obtuse.

*Leaf apex.*-Acute.

*Leaf margins.*—Serrate.

*Leaf venation.*—Pinnate, color; upper surface 144B, lower surface 145A.

*Leaf size.*—An average of 10 cm in length and 5 cm in width.

*Leaf attachment.*—Petiolate.

*Leaf number.*—An average of 16 per lateral stem.

*Leaf surface.*—Both surfaces matte, pubescent.

*Leaf color.*—Young upper surface; 187B, changing to 187A, margins and apex 187D,, young lower surface; N186C, margins 187C, flushed with 137B, mature upper surface; between 137A to 137B and N155C, 36B and 185B at the margins, mature lower surface; 137C and 187C, margins 185B.

*Petioles.*—Average of 1.3 cm in length, 3 mm in diameter, slightly pubescent and slightly glossy surfaces, both surfaces 144A with a hint of 187B in color.

Inflorescence description:

*Inflorescence type.*—Flattened, typical lace-cap, comprised of sterile and fertile flowers.

*Lastingness of inflorescence.*—Sterile flowers; persistent for an average of 6 weeks, fertile flowers; self-cleaning, an average of 5 days.

*Inflorescence number.*—One per lateral stem.

*Inflorescence size.*—An average of 8 cm in height and 4 cm in diameter.

*Flower number.*—An average of 70 sterile flowers and 90 fertile flowers.

*Flower fragrance.*—None.

*Flower aspect.*—Sterile flowers; upright, outward to slightly drooping when fading, fertile flowers; held upright.

*Flower size.*—Sterile flowers; up to 3 cm in diameter and 3 mm in depth, fertile flowers; an average of 5 mm in diameter and 3 mm in depth.

*Flower type.*—Sterile flowers rotate, fertile flowers rotate with petals drop when mature.

*Flower buds.*—Sterile flowers; an average of 2 mm in length and diameter, round, color; 145A and 61C, fertile flowers; an average of 2.5 mm in length and diameter, round, color; 63B.

*Peduncles.*—Primary peduncles; strong, flattened oval in shape, an average of 2.5 cm in length and 3 mm in width. secondary peduncles 1 cm in length and 2 mm in width, color 146D and tinged with a color between 75C to 75D, surface covered with a thin pubescence; average of 0.2 mm in length and too small to measure color.

*Pedicels*.—Sterile and fertile flowers; an average of 1 cm in length and 1 mm in width, 65C in color, surface covered with thin pubescence; average of 0.2 mm in length and too small to measure color.

*Petals*.—Sterile flowers; average of 4, rotate, ovate in shape, acute apex, acute base, entire margins, 1.1 cm in length and width, both surfaces glabrous, matte, color when opening and fully open upper and lower surface 61A to 64C and N155A towards the base, fertile flowers; average of 5, rotate, ovate to concave in shape, acute apex, cuneate base, entire margins, 2.5 mm in length and 1 mm in width, both surfaces are glabrous and smooth, color when opening and fully open upper and lower surface 63B to 63C.

*Sepals*.—Sterile flowers; 5, rotate, ovate in shape, apex is acute, base is truncate, entire margins, 1 mm in length and width, both surfaces glabrous, NN155A in color, fertile flowers; average of 5, rotate, ovate in shape, acute apex, truncate base, entire margins, 2.5 mm in length, 1 mm in width, both surfaces glabrous, 145A in color.

Reproductive organs:

*Gynoecium*.—Sterile flowers; 2 pistils, average of 1 mm in length, stigma is club-shaped, N187D, style 0.6 mm in length, NN155A in color, ovary N155A in color, fertile flowers; 3 pistils, an average of 1 mm in length, stigma; club-shaped and 155C in color, style; 1 mm in length, NN74D in color, ovary is 75C in color.

*Androecium*.—Sterile flowers; an average of 9 stamens, filaments; an average of 1 mm in length and NN155A in color, anthers; oblong in shape, an average of 0.5 mm in length and NN155A in color, pollen; low in quantity and 4D in color, fertile flowers; an average of 10 stamens, filaments; an average of 7 mm in length and NN155A in color, anthers; double broadly oblong in shape, an average of 0.8 mm in length and NN155A in color, pollen; moderate to high in quantity and 155A in color.

*Fruit and seed*.—None observed to date.

It is claimed:

1. A new and distinct cultivar of *Hydrangea* plant named 'Naga 4' substantially as herein illustrated and described.

* * * * *